(12) United States Patent
Hestad et al.

(10) Patent No.: US 8,029,544 B2
(45) Date of Patent: Oct. 4, 2011

(54) SPINE STIFFENING DEVICE

(75) Inventors: Hugh D. Hestad, Edina, MN (US); John Otte, St. Anthony, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1311 days.

(21) Appl. No.: 11/618,943

(22) Filed: Jan. 2, 2007

(65) Prior Publication Data
US 2009/0012562 A1   Jan. 8, 2009

(51) Int. Cl.
*A61B 17/70* (2006.01)
(52) U.S. Cl. ......... 606/254; 606/255; 606/257; 606/263
(58) Field of Classification Search ........... 606/250–263
See application file for complete search history.

(56) References Cited

U.S. PATENT DOCUMENTS

| | | |
|---|---|---|
| 2,296,793 A | 9/1942 | Kirschbaum |
| 2,840,070 A | 6/1958 | Tofflemire |
| 4,052,980 A | 10/1977 | Grams et al. |
| 4,226,228 A | 10/1980 | Shin et al. |
| 4,337,763 A | 7/1982 | Petrassevich |
| 4,562,832 A | 1/1986 | Wilder et al. |
| 4,597,030 A | 6/1986 | Brody et al. |
| 4,784,150 A | 11/1988 | Voorhies et al. |
| 4,945,896 A | 8/1990 | Gade |
| 5,030,220 A | 7/1991 | Howland |
| 5,035,232 A | 7/1991 | Lutze et al. |
| 5,159,921 A | 11/1992 | Hoover |
| 5,237,985 A | 8/1993 | Hodgson et al. |
| 5,353,786 A | 10/1994 | Wilk |
| 5,375,823 A | 12/1994 | Navas |
| 5,431,153 A | 7/1995 | Lee |
| 5,451,227 A | 9/1995 | Michaelson |
| 5,496,318 A | 3/1996 | Howland et al. |
| 5,520,611 A | 5/1996 | Rao et al. |
| 5,540,688 A | 7/1996 | Navas |

(Continued)

FOREIGN PATENT DOCUMENTS

EP   0669109   8/1995

(Continued)

OTHER PUBLICATIONS

Davis, Reginald J. and Maxwell, James H., "Dynesys LIS Surgical Technique", Dynesis® LIS Less Invasive Surgery, The Dynamic Stabilization System, 2005, Zimmer Spine, Inc., 24 pgs.

(Continued)

*Primary Examiner* — Eduardo C Robert
*Assistant Examiner* — Mary Hoffman
(74) *Attorney, Agent, or Firm* — Seager Tufte & Wickhem LLC

(57) ABSTRACT

In various embodiments, a spinal stabilization system has a first and a second vertebral anchor each adapted to be coupled to one of a first and a second vertebrae. The system also includes a flexible connecting element coupled to each of the first and second vertebral anchors and extending between the vertebral anchors. The connecting element has a central member and a brace positioned about the central member and the central member is stiffer than the brace to provide the needed combination of support and stiffness to the construct while offering flexibility. These and other various embodiments of this invention offer an improvement over known systems by providing stabilization of the vertebral column while allowing for flexibility and axial dampening.

8 Claims, 5 Drawing Sheets

U.S. PATENT DOCUMENTS

| | | | |
|---|---|---|---|
| 5,558,622 A | 9/1996 | Greenberg |
| 5,562,660 A | 10/1996 | Grob |
| 5,569,258 A | 10/1996 | Gambale |
| 5,584,831 A | 12/1996 | McKay |
| 5,611,800 A | 3/1997 | Davis et al. |
| 5,645,599 A | 7/1997 | Samani |
| 5,653,713 A | 8/1997 | Michelson |
| 5,725,582 A | 3/1998 | Bevan et al. |
| 5,755,660 A | 5/1998 | Tyagi |
| 5,836,948 A | 11/1998 | Zucherman et al. |
| 5,928,139 A | 7/1999 | Koros et al. |
| 5,928,140 A | 7/1999 | Hardten |
| 5,961,516 A | 10/1999 | Graf |
| 5,967,971 A | 10/1999 | Bolser |
| 6,042,538 A | 3/2000 | Puskas |
| 6,048,342 A | 4/2000 | Zucherman et al. |
| 6,080,105 A | 6/2000 | Spears |
| 6,139,493 A | 10/2000 | Koros et al. |
| 6,142,997 A | 11/2000 | Michelson |
| 6,193,651 B1 | 2/2001 | DeFonzo |
| 6,196,968 B1 | 3/2001 | Rydin et al. |
| 6,210,325 B1 | 4/2001 | Bartie et al. |
| 6,228,024 B1 | 5/2001 | Co et al. |
| 6,235,030 B1 | 5/2001 | Zucherman et al. |
| 6,241,730 B1 | 6/2001 | Alby |
| 6,263,133 B1 | 7/2001 | Hamm |
| 6,290,700 B1 | 9/2001 | Schmotzer |
| 6,322,499 B1 | 11/2001 | Evans et al. |
| D458,680 S | 6/2002 | Engler |
| 6,419,676 B1 | 7/2002 | Zucherman et al. |
| 6,428,473 B1 | 8/2002 | Leonard et al. |
| 6,440,169 B1 | 8/2002 | Elberg et al. |
| 6,451,019 B1 | 9/2002 | Zucherman et al. |
| 6,461,359 B1 | 10/2002 | Tribus et al. |
| 6,468,206 B1 | 10/2002 | Hipps et al. |
| 6,482,153 B1 | 11/2002 | Hipps et al. |
| 6,520,979 B1 | 2/2003 | Loubens et al. |
| 6,530,929 B1 | 3/2003 | Justis et al. |
| 6,554,768 B1 | 4/2003 | Leonard |
| 6,575,977 B1 | 6/2003 | Michelson |
| 6,582,433 B2 | 6/2003 | Yun |
| 6,591,049 B2 | 7/2003 | Williams et al. |
| 6,676,706 B1 | 1/2004 | Mears et al. |
| 6,743,257 B2 | 6/2004 | Castro |
| 6,793,656 B1 | 9/2004 | Mathews |
| 6,986,771 B2 | 1/2006 | Paul et al. |
| 6,989,011 B2 | 1/2006 | Paul et al. |
| 7,326,210 B2 | 2/2008 | Jahng et al. |
| 2002/0035366 A1 | 3/2002 | Walder et al. |
| 2002/0052603 A1 | 5/2002 | Nichols et al. |
| 2003/0095781 A1 | 5/2003 | Williams |
| 2003/0216740 A1 | 11/2003 | Michelson |
| 2003/0220547 A1 | 11/2003 | Holland et al. |
| 2004/0143169 A1 | 7/2004 | Branch et al. |
| 2005/0065516 A1 | 3/2005 | Jahng |
| 2005/0085815 A1 | 4/2005 | Harms et al. |
| 2005/0124991 A1 | 6/2005 | Jahng |
| 2005/0143737 A1 | 6/2005 | Pafford et al. |
| 2005/0154390 A1 | 7/2005 | Biedermann et al. |
| 2005/0171540 A1 | 8/2005 | Lim et al. |
| 2005/0203513 A1 | 9/2005 | Jahng et al. |
| 2005/0203517 A1* | 9/2005 | Jahng et al. .......... 606/61 |
| 2005/0277928 A1 | 12/2005 | Boschert |
| 2006/0084982 A1 | 4/2006 | Kim |
| 2006/0111715 A1 | 5/2006 | Jackson |
| 2006/0142758 A1 | 6/2006 | Petit |
| 2006/0212033 A1 | 9/2006 | Rothman et al. |
| 2007/0005063 A1 | 1/2007 | Bruneau et al. |
| 2007/0016200 A1 | 1/2007 | Jackson |
| 2007/0055244 A1 | 3/2007 | Jackson |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |
| 2008/0147122 A1 | 6/2008 | Jackson |

FOREIGN PATENT DOCUMENTS

| | | |
|---|---|---|
| EP | 0669109 A1 | 8/1995 |
| EP | 0669109 B1 | 5/1999 |
| EP | 1523949 A1 | 4/2005 |
| EP | 1523949 B1 | 6/2007 |
| FR | 2676911 A1 | 12/1992 |
| FR | 2715057 A1 | 7/1995 |
| FR | 2730405 A1 | 8/1996 |
| FR | 2755844 A1 | 7/2001 |
| FR | 2844180 A1 | 3/2004 |
| FR | 2867057 A1 | 9/2005 |
| WO | 9417745 A1 | 8/1994 |
| WO | WO 9519149 | 7/1995 |
| WO | 9905980 A1 | 2/1999 |
| WO | 9944527 A1 | 9/1999 |
| WO | WO 2004004549 | 1/2004 |
| WO | WO 2004024011 | 3/2004 |
| WO | 2005/037150 A1 | 4/2005 |
| WO | 2005087121 A1 | 9/2005 |
| WO | 2006066685 A1 | 6/2006 |
| WO | 2008006098 A2 | 1/2008 |

OTHER PUBLICATIONS

Humke et al., "Translaminar Screw Fixation of the Lumbar and Lumbosacral Spine (A 5-Year Follow-Up)", Spine, May 15, 1998, pp. 1180-1184, vol. 23, No. 10, 1998 Lippincott-Raven Publishers.

Orthopedic Spine Surgery: Cervical Spine, Regional Orthopedic Center, Poudre Valley Hospital, Fort Collins, Colorado.

Lu et al., "Translaminar Facet Screw Placement: An Anatomic Study", American Journal of Orthopedics, Aug. 1998, pp. 550-555, vol. 27, No. 8, Department of Orthopedic Surgery, Medical College of Toledo, Ohio.

* cited by examiner

SPINE STIFFENING DEVICE

TECHNICAL FIELD

This invention relates generally to therapeutic and corrective devices and methods for the spine and more specifically relates to devices and methods for stiffening the spine.

BACKGROUND

The spine includes a series of joints routinely called motion segment units, which is the smallest component of the spine that exhibits kinematic behavior characteristic of the entire spine. The motion segment unit is capable of flexion, extension, lateral bending and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. The purpose of fusion or rigid stabilization is the immobilization of a motion segment unit. Thus, fusion or rigid stabilization of one or more motion segment units may be an important element of a surgical procedure in certain cases (i.e., injuries, deformities, tumors, etc.). In other cases it is a complementary element (i.e., fusion performed due to degeneration).

One current spinal surgical technique typically involves fusing one or more unstable motion segment units and possibly, the removal of ligaments, bone, disc, or combinations thereof included in the unstable motion segment unit or units prior to fusing. However, fusion often involves several disadvantages. For example, the fusing process results in a permanent or rigid internal fixation of all or part of the intervertebral joints and usually involves metallic rods, plates, and the like for stabilization. Such systems are intended to rigidly immobilize the motion segment unit to promote fusion within that motion segment unit resulting in a loss of mobility.

Fusion also causes the mobility of the motion segment to be transferred to other motion segments of the spine. The added stresses transferred to motion segments neighboring or nearby the fused segment can cause or accelerate degeneration of those segments. Another disadvantage of fusion is that it is an irreversible procedure.

Spinal fixation systems using orthopedic rods as described above provide a relatively rigid construct. Another type of spinal treatment technique offers dynamic stabilization for the spine. One example of a dynamic stabilization system is provided by the assignee of this invention under the trademark DYNESYS® as generally described in European Patent Application No. 0669109A1 which is hereby incorporated by reference in its entirety. Such a dynamic stabilization system utilizes pedicle screws installed into appropriate locations in adjacent vertebrae. Flexible materials in conjunction with the pedicle screws are used rather than rigid orthopedic rods or bone grafts alone as an adjunct fusion. A tubular spacer is positioned between the pedicle screws on adjacent vertebrae with a tensioned cord passing through the central lumen of the spacer. Dynamic stabilization systems of this type bring the lumbar vertebrae into a desired anatomical position while stabilizing the effective segments and without irreversible fusion.

Fusion procedures can be improved by modifying the load sharing characteristics of the treated spine and one technique is to allow more of a physiologic loading between pedicular fixation and anterior column support. Additionally, a device and associated method that precludes or at least delays the need for fusion for all but the most advanced degeneration of a motion segment, particularly if such a device would allow close to normal motion and pain relief is desirable. Moreover, utilization of minimally invasive surgical procedures and techniques to install such devices is also a highly desirable objective to enhance and promote patient healing and recovery.

SUMMARY OF THE INVENTION

This invention addresses these and other shortcomings in the prior art. In various embodiments, the invention includes a spinal stabilization system having a first and a second vertebral anchor each adapted to be coupled to one of a first and a second vertebrae. The system also includes a flexible connecting element coupled to each of the first and second vertebral anchors and extending between the vertebral anchors. The connecting element has a central member and a brace positioned about the central member and the central member is stiffer than the brace to provide the needed combination of support and stiffness to the construct while offering flexibility.

In other embodiments of this invention, the spinal stabilization construct includes first and a second top loading polyaxial pedicle screw each adapted to be coupled to one of a first and a second vertebrae. The construct also includes a flexible connecting element coupled to each of the first and second pedicle screws and extending between the pedicle screws. The connecting element has a central member. A first and a second securing member are each threadably coupled to one of the pedicle screws to secure the connecting element thereto. A brace is positioned concentrically about the central member and the central member is stiffer than the brace. A first and a second shank extend in opposite directions from the central member and each shank is coupled to one of the pedicle screws. A first and a second flange are on the connecting element and the flanges are spaced on opposite sides of the brace.

The spinal stabilization system may also include a third and a fourth flange on the connecting element, each of which are spaced on opposite sides of the central member, embedded in the brace and spaced from the first and second flanges.

Other embodiments of a spinal stabilization system according to this invention include a first and a second vertebral anchor each adapted to be coupled to one of a first and a second vertebrae and a flexible connecting element coupled to each of the first and second vertebral anchors and extending between the vertebral anchors. The connecting element has a central member and a brace positioned about the central member. A first and a second flange are each on the connecting element and spaced on opposite sides of the brace. The system may also include a first and a second shank extending in opposite directions from the first and second flanges, respectively. Each shank is coupled to one of the vertebral anchors. A third and a fourth flange may be included on the connecting element and spaced on opposite sides of the central member, embedded in the brace and spaced from the first and second flanges. The first and second flanges may be integrally formed with the first and second shanks, respectively.

In another embodiment of this invention, the spinal stabilization includes a first and a second polyaxial pedicle screw each adapted to be coupled to one of a first and a second vertebrae. A flexible connecting element is coupled to each of the first and second polyaxial pedicle screws and extends between the pedicle screws. A first and a second securing member are each threadably coupled to one of the pedicle screws to secure the connecting element thereto. The flexible connecting element may be integrally formed from a polymeric, elastomeric or non-metallic material.

These and other various embodiments of this invention offer an improvement over known systems by providing stabilization of the vertebral column while allowing for flexibility and axial dampening.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
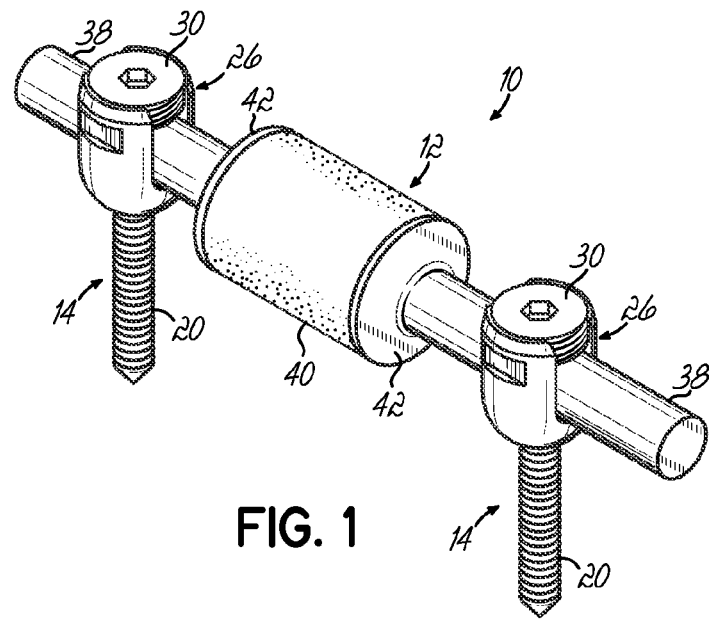
FIG. 1 is perspective view of a spinal stabilization construct according to a first embodiment of this invention.

Referring to FIG. 1, one embodiment of a spine stiffening stabilization system 10 is shown and includes a connecting element 12 coupled to and extending between a pair of vertebral anchors 14. Each vertebral anchor 14 is adapted to couple to either of two vertebras 16 in a patient's spine 18. With the connecting element 12 secured to the vertebral anchors 14, the connecting element 12 maintains a restored disc space height and/or alignment between the adjacent vertebrae 16. In one form, the connecting element 12 preserves motion between the adjacent vertebrae 16.

In one embodiment as shown in the various drawings, such as FIGS. 1, 2, 10B, and 11, the vertebral anchor 14 is a polyaxial, top loading pedicle screw including a threaded shaft 20 adapted to be inserted into a pedicle area 22 of the vertebrae 16. The vertebral anchor includes a head 24 on the threaded shaft 20 and a saddle 26 is coupled to the head 24 and is adapted for polyaxial movement of the saddle 26 relative to the shaft 20. The saddle 26 having an exemplary U-shape provides a top loading capability to the vertebral anchor 14 so that the connecting element 12 may be inserted downwardly into the saddle 26 between a pair of polyaxial head receiving arms 28. The saddle 26 can be constructed with any desired shape. A securing member in the form of a threaded set screw 30 mates with the saddle 26 to secure the connecting element 12 to the vertebral anchor 14. Each receiving arm 28 of the U-shaped saddle 26 has threads 32 which mate with the threads 34 on the set screw securing member 30. While a top loading polyaxial pedicle screw is shown and described herein as one embodiment of the vertebral anchor 14, other types of vertebral anchors can readily be used within the scope of this invention including standard fixed pedicle screws, hooks or other devices intended to couple a connecting element to the vertebrae.

Figure 2:
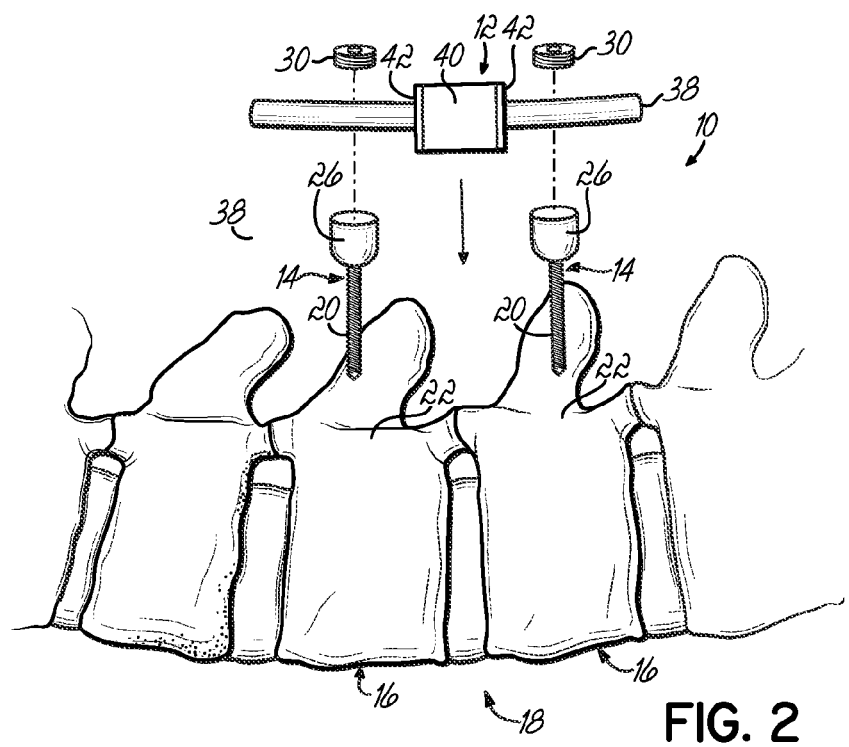
FIG. 2 is a side elevational view of the system of FIG. 1 being installed on a patient's vertebral column.
Figure 3:
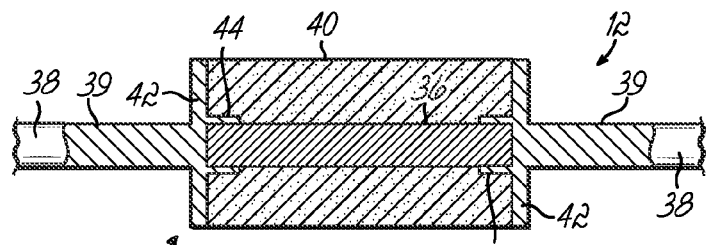
FIG. 3 is a cross-sectional view of a flexible connecting element of the embodiment of FIG. 1.

Referring to FIGS. 1-3, one embodiment of the connecting element 12 according to this invention includes a central portion or member 36 and a pair of connecting portions or shanks 38 that include rod portions 39 that can be of any suitable shape to fit within the saddle 26 extending in opposite directions on the connecting element 12. Each shank 38 is coupled to one of the vertebral anchors 14. The terminal ends of the shanks 38 of the various embodiments of this invention can be trimmed to length after sizing and installation. Alternatively, the connecting members 38 can be pre-sized prior to implementation. The central member 36 is concentrically surrounded by a flexible portion or brace 40. The brace 40 is positioned between spaced flanges 42 and the central member 36 is secured within the brace 40 and between the flanges 42 by crimping tabs 44.

The connecting element 12 of this invention includes a flexible intermediate portion 46. In one embodiment, the brace 40 and central member 36 are intended for use in the intermediate portion 46. Alternatively, a solid flexible core can be used as the flexible intermediate portion 46. In one embodiment, the brace 40 is an elastomeric member that allows for flexing of the connecting element 12. The brace 40 stabilizes the spine 18 while allowing for flexibility and axial dampening. In one embodiment, the central member 36 is tensioned and integral to the intermediate portion 46 of the connecting element 12. The central member 36 allows for bending of the shanks 38 and the associated forces on the brace 40. Unlike standard spine rods which provide little or no flexibility and axial dampening, the connecting element 12 of this invention allows for flexing of the spinal stabilization system 10 in response to movement of the vertebrae 16. The configuration and interaction of the various component parts of the connecting element 12 of FIGS. 1-3 allows for bending of the connecting element 12 and the shanks 38 connected to the vertebral anchors 14 so that the central member 36 is placed under tension and one side of the brace 40 is compressed depending upon the orientation of the bending motion.

Figure 4:
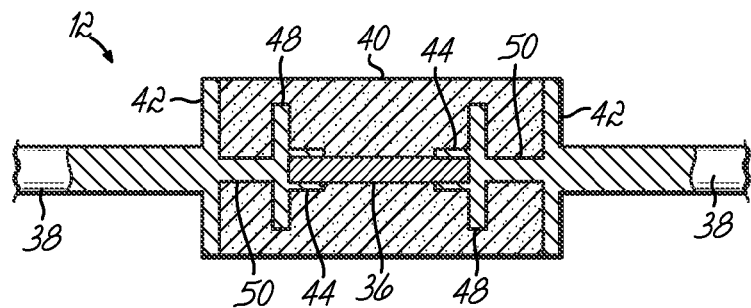
FIG. 4 is a cross-sectional view of another embodiment of a flexible connecting element according to this invention.

Referring to FIG. 4, a cross-sectional view of an alternative embodiment of the connecting element 12 according to this invention is shown in which the shanks 38 are connected to a pair of spaced outer flanges 42 between which the flexible brace 40 is positioned. The central member 36 is embedded within the brace 40 and includes an additional pair of spaced inner flanges 48 between which a portion of the central member 36 is held by mechanical crimping tabs 44 or similar arrangement. Each of the inner flanges 48 is mounted and spaced from an associated outer flange 42 by an extension 50 of the shank 38 extending into the brace 40. The embodiment of FIG. 4 allows the shanks 38 and flanges 42 when bent to apply both compressive and tensile forces to the brace 40 as well as tension to the central member 36. The central member 36 according to various embodiments of this invention may be made from a Dacron™ tape woven cord, a braided stainless steel or titanium cable, carbon fiber, Kevlar™ or a variety of other materials providing sufficient strength with low elongation characteristics. Other options for the central member 36 include a synthetic or natural rubber woven cord which is stretched between the flanges 42 prior to attachment and mounting therein. The cord would be attached to the flanges 42 and then stretched into a mold cavity where the polymer or elastomer brace material would be injected into the mold so that the central cord would be in constant tension, but below its elastic limit.

Figure 5:
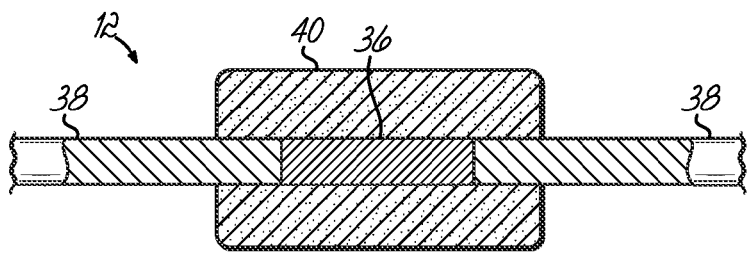
FIG. 5 is a cross-sectional view of a still further embodiment of a flexible connecting element according to this invention.

A further alternative embodiment of the connecting element 12 according to this invention is shown in FIG. 5 in which the central member 36 is surrounded by the brace 40 and oppositely extending shanks 38 mount the connecting element 12 to the respective vertebral anchors 14. The central member 36 of FIG. 5 may be en elastic mesh or woven member and the polymer material of the brace 40 would then be injection molded through the mesh and around the corded central member. The central member 36 could be steel, titanium, nickel titanium alloy, polymer, carbon fiber or other materials. In the various embodiments, the connecting element 12 is a flexible member that provides a shock absorbing effect in transmitting spinal column loads between the anchors 14 to which it is engaged. Intermediate portion 46 between the flanges 42 can also permit relative movement to allow motion of the spinal column segment to which connecting element 12 is engaged. In one embodiment, intermediate portion 46 provides connecting element 12 with a variable stiffness profile between anchors 14.

Figure 6:
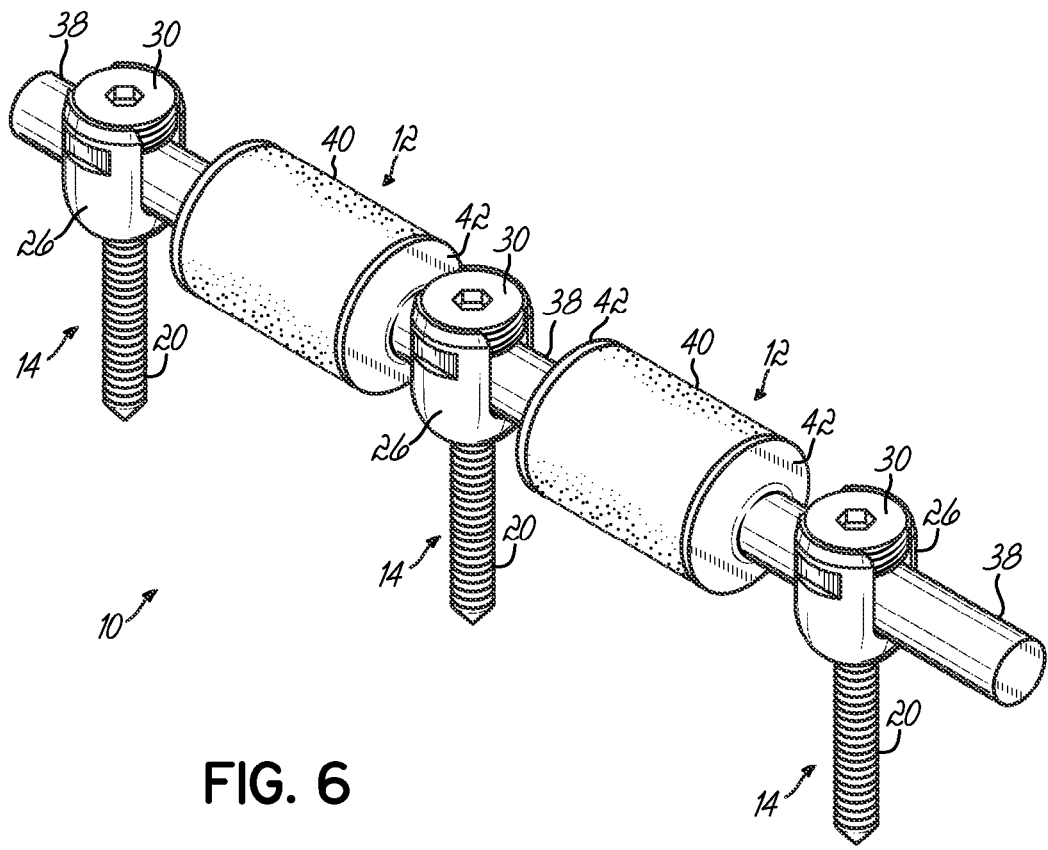
FIG. 6 is a perspective view of a multi-level spinal stabilization system according to another embodiment of this invention.

For installation requiring more than one level of treatment, a two-level section system 10 such as the embodiment shown in FIG. 6 could be utilized. The construct of FIG. 6 provides two flexible connecting elements 12 with a predetermined space between them. The length of the shank 38 positioned between the connecting elements 12 of the embodiment of FIG. 6 could be fixed or a variable distance to accommodate different vertebral anatomies.

Figure 7:
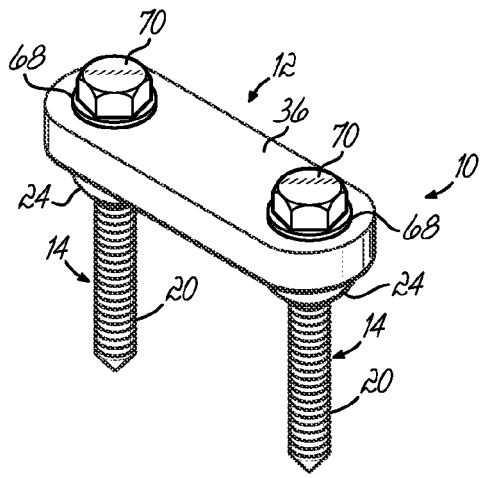
FIG. 7 is a perspective view of a still further embodiment of a flexible connecting element for use in a spinal stabilization system according to this invention.
Figure 8:
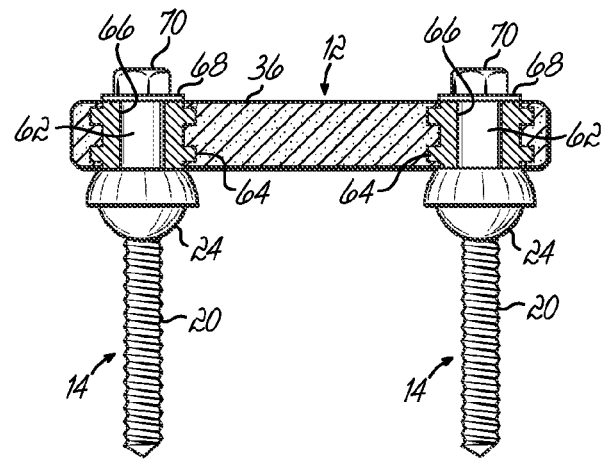
FIG. 8 is cross-sectional view of the flexible connecting element of FIG. 7.

A further alternative embodiment of a spinal stabilization stiffening system 10 according to this invention is shown in perspective view in FIG. 7 and cross-sectional view in FIG. 8. The vertebral anchor 14 of the embodiment of FIGS. 7 and 8 is shown as a pedicle screw having a threaded shaft 20 and a head 24. The vertebral anchor 14 in one embodiment is a polyaxial pedicle screw similar to a device marketed by Zimmer Spine, Inc. as the ST360™. The vertebral anchor 14 includes an upwardly extending toggle 62. The connecting element 12 is mounted to the toggles 62 of the vertebral anchors 14. The connecting element 12 in one embodiment includes a central member 36 of an elastomeric or polymeric material providing flexibility to the construct. The central member 36 is molded about a pair of rims 64 providing an aperture 66 so that the connecting element 12 may be mounted downwardly onto the toggles 62 and secured in place by a washer 68 and threaded nut 70 combination as shown in FIGS. 7 and 8.

Figure 9:
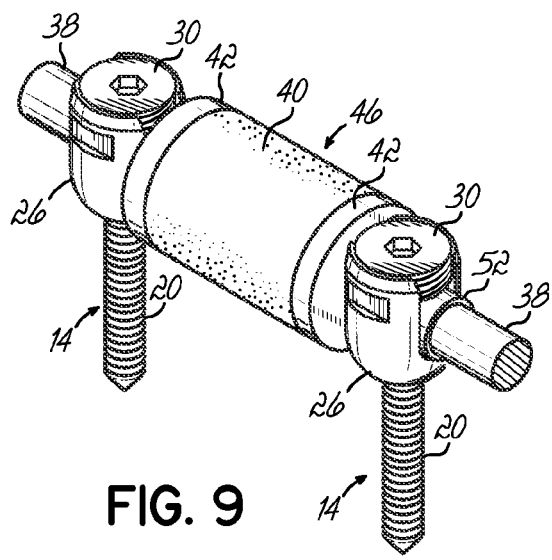
FIG. 9 is a perspective view of a still further embodiment of a flexible connecting element for use in a spinal stabilization system according to this invention.
Figure 10A:
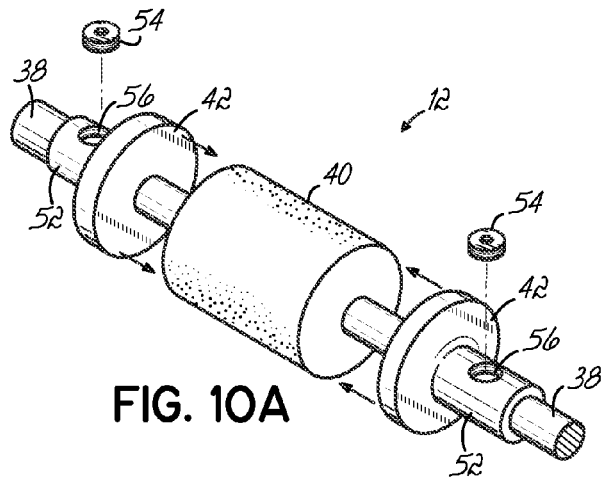
FIG. 10A is a disassembled, perspective view of the flexible connecting element of FIG. 9.
Figure 10B:
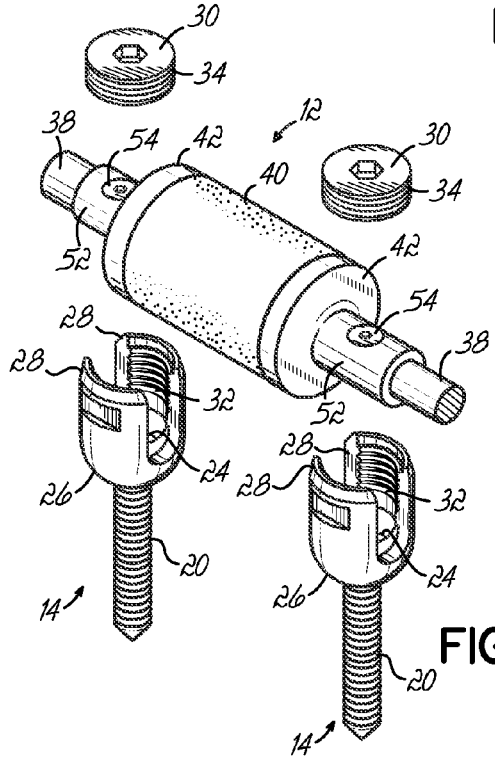
FIG. 10B is a partially disassembled view of the spinal stabilization system utilizing the flexible connecting element of FIGS. 9 and 10A.
Figure 11:
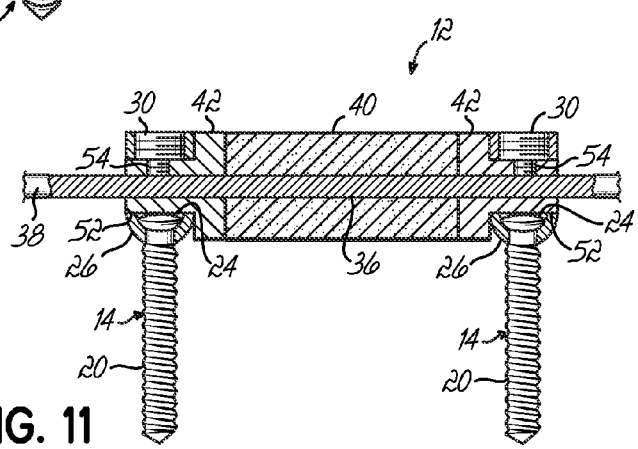
FIG. 11 is a cross-sectional view of the assembled spinal stabilization system of FIG. 10B.

Referring to FIGS. 9-11, a further alternative embodiment of the connecting element 12 according to this invention is shown. In this embodiment, flanges 38 are provided with outwardly projecting annular hubs 52 and a securing element in the form of a setscrew 54 is seated within a threaded aperture 56 on the hub 52 to secure the flange 42 and hub 52 arrangement to the shank 38 of the connecting element 12 and against the brace 40. The connecting element can be assembled pre- or intra-operatively. Once assembled, as shown in FIG. 10A, the connecting element 12 is positioned in the top loading vertebral anchors 14 and secured thereto by the vertebral anchor set screws 30 as shown in FIG. 10B resulting in the arrangement and installation of FIG. 9. In this embodiment, the intermediate portion 46 is of a different size than intermediate portion 46 of FIG. 1 and occupies more of the distance between the securing members 30. A cross-sectional view of the connecting element 12 and associated vertebral anchors 14 of FIGS. 9-10B is shown in FIG. 11.

Figure 12:
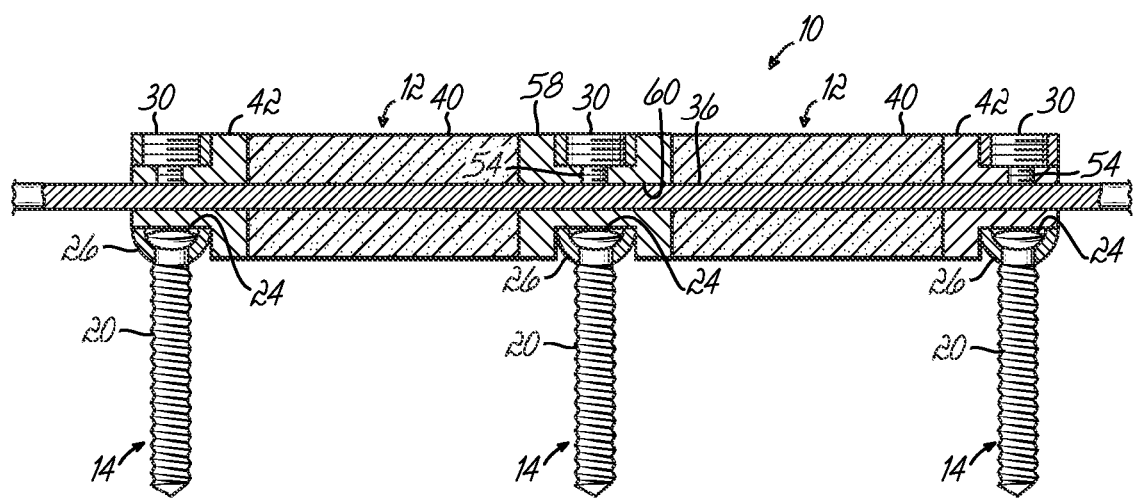
FIG. 12 is a view similar to FIG. 11 of a multi-level spinal stabilization system.

In a still further embodiment shown in FIG. 12, a multi-level construct 10 is provided with a generally H-shaped hub 58 having a duct 60 there through for the central member 36 to extend from one connecting element 12 to an adjacent connecting element 12.

The flanges 42 can be adapted to engage the flexible brace 40 there between. In one embodiment, flanges 42 include holes to receive attachment means such as fasteners, sutures, threads, wires, or other devices to engage central member 36 to the respective flange 42. In another embodiment, the brace 40 is injection molded between flanges 42. The injected material can flow into holes in the central member 36 to form around central member 36 and at least partially around the flanges 42 to provide engagement therewith. In still another embodiment, intermediate portion 46 is molded over flanges 42. In any embodiment, the connecting element 12 can be provided with or without the central member 36 and with or without the flanges 42.

In one procedure, anchor 14 is engageable to a first vertebra 16, a second anchor 14 is engageable to a second vertebra 16 and a third anchor 14 is engageable to a third vertebra 16. When so engaged, intermediate portion 46 allows the vertebrae to which the anchors 14 are engaged to move or flex relative to one another, but limits extension and flexion motion to provide a stabilizing effect.

Connecting element 12 can be guided into position between the anchors 14 using an installation instrument as discussed above. The installation instrument may include extenders extending from any one, two or three of the anchors 14. Other techniques contemplate insertion with an open surgical technique, or guiding of the connecting element 12 distally along extenders extending proximally from one or more of the anchors 14. Connecting element 12 can be employed in fusion procedures or in procedures employing dynamic stabilization without fusion. In fusion procedures, fusion promoting material and/or one or more fusion devices, implants, or bone graft are placed in the disc space between adjacent vertebrae. In such procedures, a single level connecting element 12 may be coupled between the vertebrae if dynamic stabilization is desired. If rigid stabilization is desired, an elongated connecting element 12 can be provided and engaged between the vertebrae to be fused, and one or more adjacent vertebral levels can be dynamically stabilized with the intermediate portion 46 engaged between these or more other vertebral levels.

While in the illustrated embodiments the connecting elements 12 are shown as being adapted to extend along one or two vertebral levels, the connecting elements 12 can also extend along three or more vertebral levels. For example, one of the shanks 38 can include a length that extends along multiple vertebral levels to be fused to provide rigid stabilization of these levels, while the other of the shanks 38 includes a length adapted to extend along at least one vertebral level to provide a flexible intermediate portion 46 between vertebrae 16 for dynamic stabilization.

The flexible brace 40 discussed herein can be made from any suitable material allowing at some motion of the vertebral level along which the intermediate portion 46 is engaged. For example, the brace portions 40 can be made from elastomers, polycarbonateurethane, polyetheretherketone, or other polymer material. The brace 40 can be made from resorbable material. In still another form, the brace 40 include springs, which can be made from metal or other suitable material.

It is further contemplated that the connecting element 12 can be provided with a varying stiffness profiles to vary the stiffness properties of the system 10 and control movement of the one or more dynamically stabilized vertebral levels. Such varying stiffness profiles can be provided across the cross-section of a single flexible intermediate portion 46 of a particular connecting element 12, or provided between different intermediate portions 46 of a single multi-level connecting element 12, or provided between a number of connecting elements 12 in a kit where the connecting elements 12 includes one or more portions with a stiffness profile that varies relative to one or more of the portions of the other connecting elements 12.

In one embodiment, the hardness characteristics of the material comprising the flexible brace 40 is varied. For example, the durometer of an elastomer material comprising the one or more flexible brace portions 40 may vary to allow selection and implantation of a connecting element 12 providing the desired motion characteristics for the vertebral level.

In another embodiment, the connecting element 12 is provided with a central member 36 that couples the first and second flanges 42 to one another through the flexible brace portion 40. The diameter of the central member 36 can be varied so that the connecting elements 12 with flexible brace portions 40 extending about a central member 36 with a greater diameter are stiffer than connecting elements 12 with a flexible brace portion 40 extending about a central member 36 of lesser diameter.

In a further embodiment, the central member 36 can be pre-tensioned so that the flanges 42 are compressed against the flexible brace portion 40 when engaged thereto. The amount of pre-tension can range from zero to the tensile break strength of the central member 36. The greater pre-tension loading of the central member 36 results in stiffer flexible brace portion 40 behavior since the preloading compresses the flexible brace portion 40 between the flanges 42.

From the above disclosure of the general principles of the invention and the preceding detailed description of at least one embodiment, those skilled in the art will readily comprehend the various modifications to which this invention is susceptible. Therefore, we desire to be limited only by the scope of the following claims and equivalents thereof.

We claim:

1. A spinal stabilization system comprising:
    a first and a second vertebral anchor each adapted to be coupled to one of a first and a second vertebrae, each vertebral anchor including a U-shaped channel defined between first and second receiving arms;
    a flexible connecting element coupled to each of the first and second vertebral anchors and extending between the vertebral anchors, the connecting element including a central member;
    a brace positioned about the central member;
    a first and a second flange on the connecting element, the flanges being spaced on opposite sides of the brace;
    a first and a second shank extending in opposite directions from the first and second flanges, respectively, the first shank being coupled in the U-shaped channel of the first vertebral anchor with a first securing member threadedly engaging threads of both receiving arms of the first vertebral anchor and the second shank being coupled in the U-shaped channel of the second vertebral anchor with a second securing member threadedly engaging threads of both receiving arms of the second vertebral anchor;
    a third securing element engaging the central member to secure the central member to the first shank.

2. The spinal stabilization system of claim 1, further comprising a fourth securing element engaging the central member to secure the central member to the second shank.

3. The spinal stabilization system of claim 1, wherein the first and second flanges are integrally formed with the first and second shanks, respectively.

4. The spinal stabilization system of claim 1, wherein the brace is a polymeric, elastomeric or non-metallic material.

5. The spinal stabilization system of claim 1, wherein the brace is positioned concentrically around the central portion.

6. The spinal stabilization system of claim 1, wherein a third vertebral anchor is positioned intermediate the first and second vertebral anchors and adapted to be coupled to a third vertebrae; and
    a hub coupled to the third vertebral anchor and the connecting element.

7. The spinal stabilization system of claim 6 wherein the hub further comprises:
    a third and a fourth flange positioned on opposite sides of the third vertebral anchor; and
    a duct formed in the hub, the central member of the connecting element extending through the duct.

8. The spinal stabilization system of claim 6, wherein the brace is positioned on a first side of the hub and a second brace positioned about the central member is positioned on a second side of the hub.

* * * * *